US010433934B2

(12) United States Patent
Kopelman

(10) Patent No.: US 10,433,934 B2
(45) Date of Patent: Oct. 8, 2019

(54) ADJUSTING A TOOTH POSITION

(71) Applicant: Align Technology, Inc., San Jose, CA (US)

(72) Inventor: Avi Kopelman, Palo Alto, CA (US)

(73) Assignee: Align Technology, Inc., San Jose, CA (US)

(*) Notice: Subject to any disclaimer, the term of this patent is extended or adjusted under 35 U.S.C. 154(b) by 79 days.

(21) Appl. No.: 15/607,042

(22) Filed: May 26, 2017

(65) Prior Publication Data

US 2017/0258555 A1 Sep. 14, 2017

Related U.S. Application Data

(63) Continuation of application No. 13/913,317, filed on Jun. 7, 2013, now Pat. No. 9,675,427.

(51) Int. Cl.
*A61C 7/08* (2006.01)

(52) U.S. Cl.
CPC ........... *A61C 7/08* (2013.01); *Y10T 29/49568* (2015.01)

(58) Field of Classification Search
CPC ........... A61C 7/00–08; Y10T 29/49568; Y10T 29/49569
USPC ................. 433/6, 24; 128/848, 861
See application file for complete search history.

(56) References Cited

U.S. PATENT DOCUMENTS

| | | | |
|---|---|---|---|
| 3,092,907 A | 6/1963 | Traiger | |
| 4,505,672 A | 3/1985 | Kurz | |
| 4,523,908 A | 6/1985 | Drisaldi et al. | |
| 5,683,244 A * | 11/1997 | Truax | A61C 7/00 433/24 |
| 6,230,142 B1 | 5/2001 | Benigno et al. | |
| 6,572,372 B1 | 6/2003 | Phan et al. | |
| 6,983,752 B2 * | 1/2006 | Garabadian | A61F 5/566 128/848 |
| 8,136,529 B2 * | 3/2012 | Kelly | A61F 5/566 128/848 |
| 8,292,617 B2 | 10/2012 | Brandt et al. | |
| 8,517,726 B2 | 8/2013 | Kakavand et al. | |
| 2003/0198911 A1 | 10/2003 | Knopp et al. | |
| 2005/0233276 A1 * | 10/2005 | Kopelman | A61C 7/08 433/3 |
| 2007/0065768 A1 | 3/2007 | Nadav | |
| 2008/0062429 A1 | 3/2008 | Liang et al. | |
| 2008/0169122 A1 | 7/2008 | Shiraishi et al. | |

(Continued)

FOREIGN PATENT DOCUMENTS

DE 202012011899 U1 1/2013
JP 2007537824 A 12/2007

OTHER PUBLICATIONS

International Search Report and Written Opinion of international application No. PCT/IB2014/000951, dated Sep. 25, 2014, 12 pp.

(Continued)

*Primary Examiner* — Yogesh P Patel
(74) *Attorney, Agent, or Firm* — Shay Glenn LLP

(57) ABSTRACT

The present disclosure provides methods, devices, and systems for adjusting a tooth position. A system for adjusting a tooth position can include an attachment configured to be attached to a tooth to be moved, a dental appliance including a guide slot configured to receive the attachment and to define an adjustment trajectory of the tooth, and an adjustment band to generate force on the tooth to move the tooth along the adjustment trajectory.

20 Claims, 10 Drawing Sheets

(56) References Cited

U.S. PATENT DOCUMENTS

| | | | |
|---|---|---|---|
| 2009/0170050 A1* | 7/2009 | Marcus | A61B 17/6433 |
| | | | 433/18 |
| 2009/0191502 A1* | 7/2009 | Cao | A61C 7/002 |
| | | | 433/24 |
| 2010/0015565 A1* | 1/2010 | Carrillo Gonzalez | A61C 5/00 |
| | | | 433/7 |
| 2011/0065060 A1 | 3/2011 | Teixeira et al. | |
| 2011/0136090 A1 | 6/2011 | Kazemi | |
| 2011/0269092 A1* | 11/2011 | Kuo | A61C 7/002 |
| | | | 433/6 |
| 2013/0089828 A1 | 4/2013 | Borovinskih et al. | |
| 2013/0150689 A1 | 6/2013 | Shaw-Klein | |
| 2014/0178829 A1* | 6/2014 | Kim | A61C 7/36 |
| | | | 433/3 |
| 2014/0186794 A1 | 7/2014 | Deichmann et al. | |
| 2015/0216716 A1* | 8/2015 | Anitua Aldecoa | A61F 5/566 |
| | | | 128/848 |
| 2016/0022185 A1 | 1/2016 | Agarwal et al. | |

OTHER PUBLICATIONS

Dentalwings; Intraoral scanner; 7 pages; retrieved from the internet (https://web.archive.org/web/20160422114335/http://www.dentalwings.com/products/intraoral-scanner/); available as of Apr. 4, 2016.

Dentalwings; I series dental impression scanner; 8 pages; retrieved from the Internet (https://web.archive.org/web/20160502145908/http://www.dentalwings.com/products/scan-and-design-systems/iseries/); available as of May 2, 2016.

* cited by examiner

ADJUSTING A TOOTH POSITION

PRIORITY INFORMATION

This application is a Continuation of U.S. application Ser. No. 13/913,317, filed Jun. 7, 2013, the entire contents of which are hereby incorporated by reference.

BACKGROUND

The present disclosure is related to methods, devices, and systems for adjusting a tooth position. Dental treatments, such as those in the orthodontic field may include repositioning misaligned teeth and changing bite configurations for improved cosmetic appearance and/or dental function. Repositioning can be accomplished, for example, by applying controlled forces to one or more teeth over a period of time.

As an example, repositioning may be provided through a process that uses one or more positioning appliances that are utilized for aligning teeth. Such appliances may, for example, utilize a thin shell of material having resilient properties, referred to as a "shell" or an "aligner," that generally conforms to a patient's teeth but is slightly out of alignment with a current tooth configuration.

Placement of such an appliance over the teeth may provide controlled forces in specific locations to gradually move one or more teeth into a new configuration. Repetition of this process with successive appliances in progressive configurations can move the teeth through a series of intermediate arrangements to a final desired arrangement.

Such systems typically utilize materials that are light weight and/or transparent to provide a set of appliances that can be used serially such that, as the teeth move, a new appliance can be implemented to further move the teeth.

DETAILED DESCRIPTION

Figure 1:
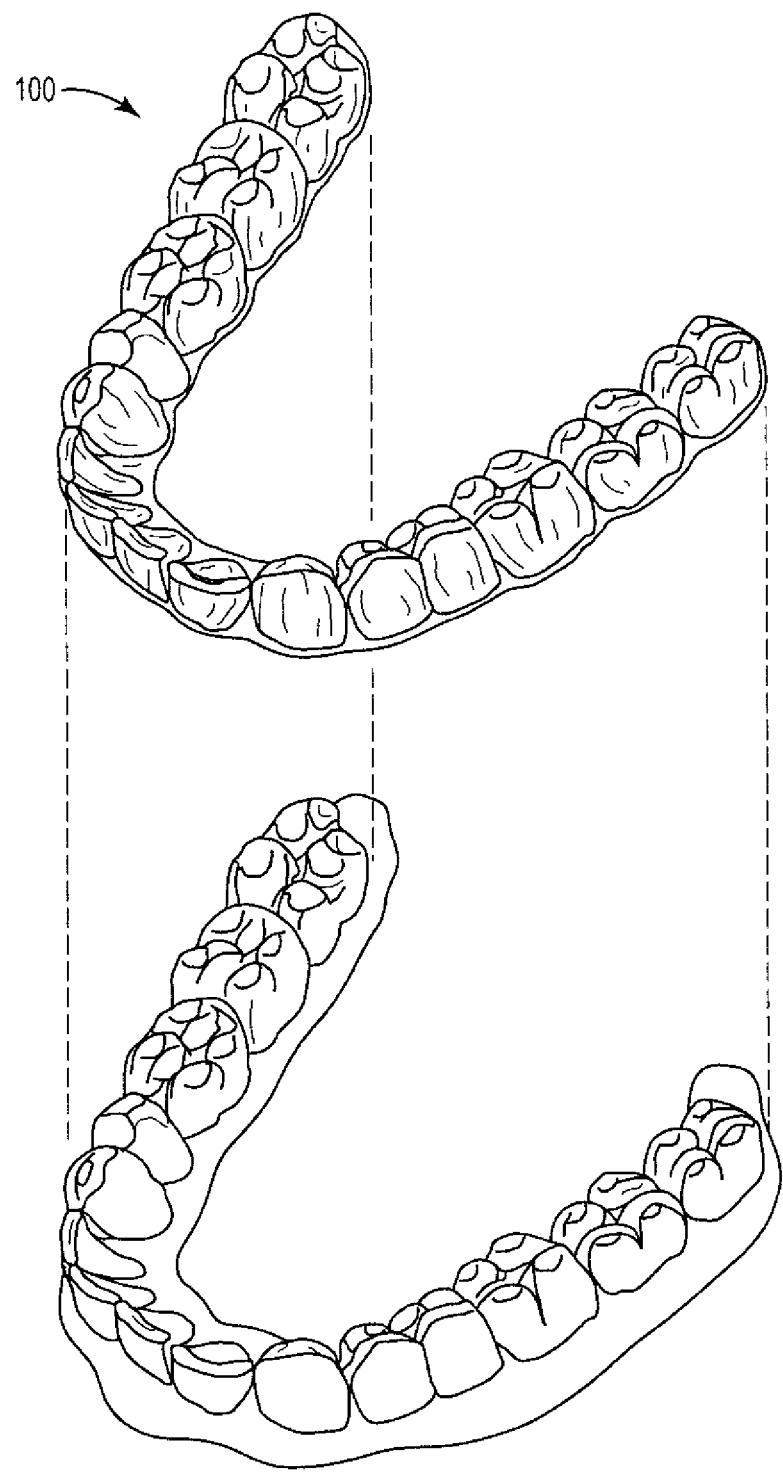
FIG. 1 illustrates a jaw of teeth together with a shell according to a number of embodiments of the present disclosure.

As discussed above, the present disclosure provides methods, devices, and systems for adjusting a tooth position. Generally, such adjustments occur during an orthodontic treatment which is a process of moving and reorienting teeth for functional and/or aesthetic purposes, although adjustments may be made for other purposes.

Prior approaches to tooth adjustment, such as those performed during orthodontic treatment include a having treatment professional place a variety of orthodontic components including brackets, which are firmly fixed to the teeth, and other components including wires, tensioning springs, etc., which apply forces and moments on the teeth, through the brackets, thereby causing the teeth to move. Prior approaches also include the use of brackets, wires, and/or elastics to move a tooth along a wire. The wire can act as a guide or "rail" to limit the trajectory of movement of a tooth. Tooth anchoring during tooth adjustment with a bracket system can create challenges including undesired movement of an anchor tooth or attachment, for example.

Approaches for adjusting a position of a tooth (e.g., repositioning teeth in a patient's jaw) according to embodiments of the present disclosure include utilizing a set of one or more adjustment appliances such as positioners, retainers, and/or other removable appliances (e.g., clear shells and/or aligners) having a shell to be worn over the teeth of a patient and having a guide slot formed therein for guiding an attachment that is positioned on a tooth and thereby guiding the movement of the tooth.

A plurality of appliances can be worn by a patient successively to achieve gradual tooth repositioning with at least one appliance having a guide slot formed therein. In embodiments of the present disclosure, adjusting a position of a tooth can include utilizing a shell with a guide slot in conjunction with adjustment bands to make tooth body movements (e.g., move an entire tooth without tipping of a crown and/or root of a tooth). In some examples, an arch of a patient's jaw can be used as an anchor, which can allow for a tooth to move or a group of teeth to move as a group, within the shell, in contrast to prior bracket system approaches.

In a number of embodiments of the present disclosure, adjusting a tooth position can include one or more orthodontic or dental applications, such as: adjusting and/or moving a tooth to close a space between teeth, adjusting and/or moving a tooth to achieve target interproximal contacts, adjusting and/or moving a tooth to provide space for an implant, adjusting and/or moving a tooth to provide space for an un-erupted tooth, adjusting and/or moving a tooth in a target trajectory, and/or uprighting, extruding, adjusting, and/or moving a tooth to a target (e.g., predefined) location, among others.

For example, in some embodiments, a system for adjusting a tooth position can include: a number of attachments configured to be attached to a number of teeth targeted to be adjusted, a dental appliance including a guide slot configured to adapt to the number of attachments and to define an adjustment trajectory of the number of teeth, and an adjustment band to generate force on the number of teeth to adjust the number of teeth along the adjustment trajectory.

In the detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure. As used herein, the designator "N", particularly with respect to reference numerals in the drawings, indicates that a number of the particular feature so designated can be included. As used herein, "a number of" a particular thing can refer to one or more of such things (e.g., a number of teeth can refer to one or more teeth).

The figures herein follow a numbering convention in which the first digit or digits correspond to the drawing figure number and the remaining digits identify an element or component in the drawing. Similar elements or components between different figures may be identified by the use of similar digits. For example, 207 may reference element "07" in FIG. 2, and a similar element may be referenced as 407 in FIG. 4. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

FIG. 1 illustrates a jaw together with a shell 100 (e.g., incremental position adjustment appliance) according to a number of embodiments of the present disclosure. Shell 100 can, for example, comprise a polymeric shell having a cavity shaped to receive and resiliently reposition teeth from one tooth arrangement to another tooth arrangement.

The shell can fit over all or some teeth present in the upper or lower jaw. In some examples, one, some, or all of the teeth can be repositioned while others can provide a base or anchor for holding the repositioning appliance in place as it applies resilient repositioning force against the tooth or teeth to be repositioned. The gingiva and the palette can also serve as anchors in some cases, (e.g., through interaction with an upper and/or lower dental arch) allowing all or nearly all of the teeth to be repositioned simultaneously.

Shell 100 can, for example, be formed from a thin sheet of a suitable elastomeric polymer. In a number of examples, no wires or other mechanisms are provided for holding the appliance in place over the teeth. However, as will be described further herein, individual attachments can be provided on the teeth with corresponding receptacles or apertures in the shell so that the shell can be held onto the teeth and/or so the shell and/or one or more adjustment bands can apply forces to the teeth.

Figure 2A:
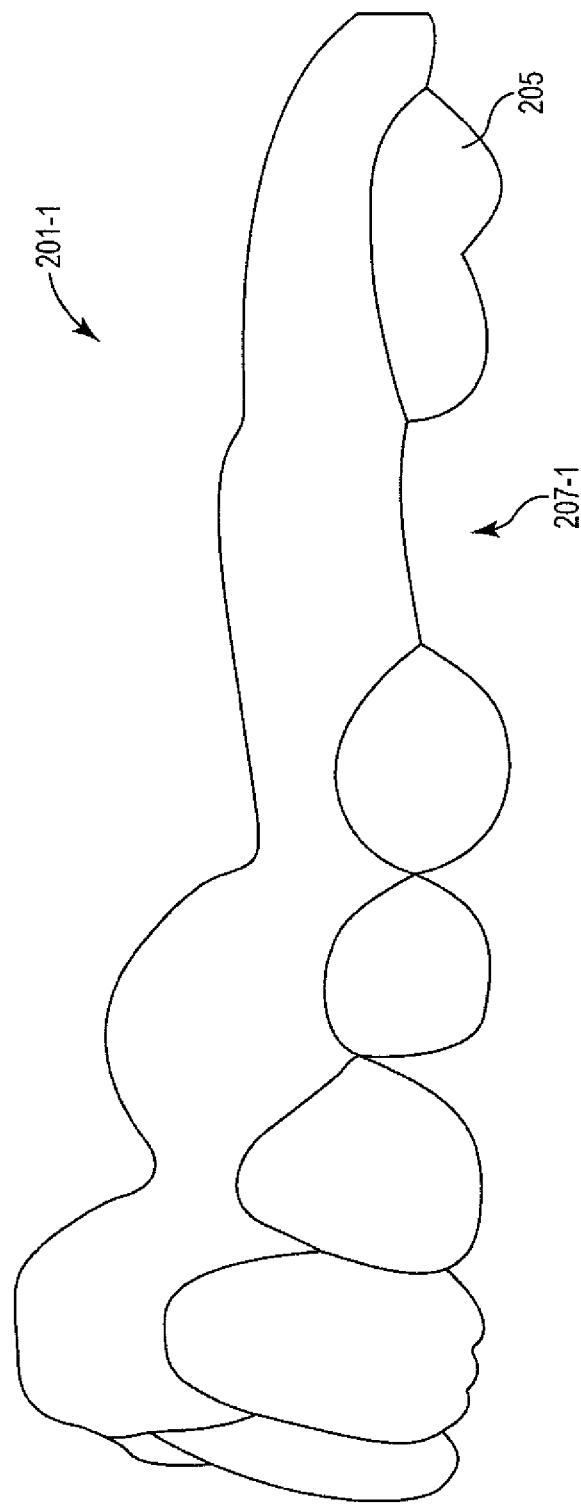
FIGS. 2A-2D illustrate an example system and device for adjusting a tooth position according to a number of embodiments of the present disclosure.

FIGS. 2A-2D illustrate an example system and device for adjusting a tooth position according to a number of embodiments of the present disclosure. FIG. 2A illustrates an upper jaw 201-1 including a space that is to be closed 207-1 (e.g., missing tooth). In a number of embodiments, tooth 205 can be adjusted (e.g., mesially) to close space 207-1.

Figure 2B:
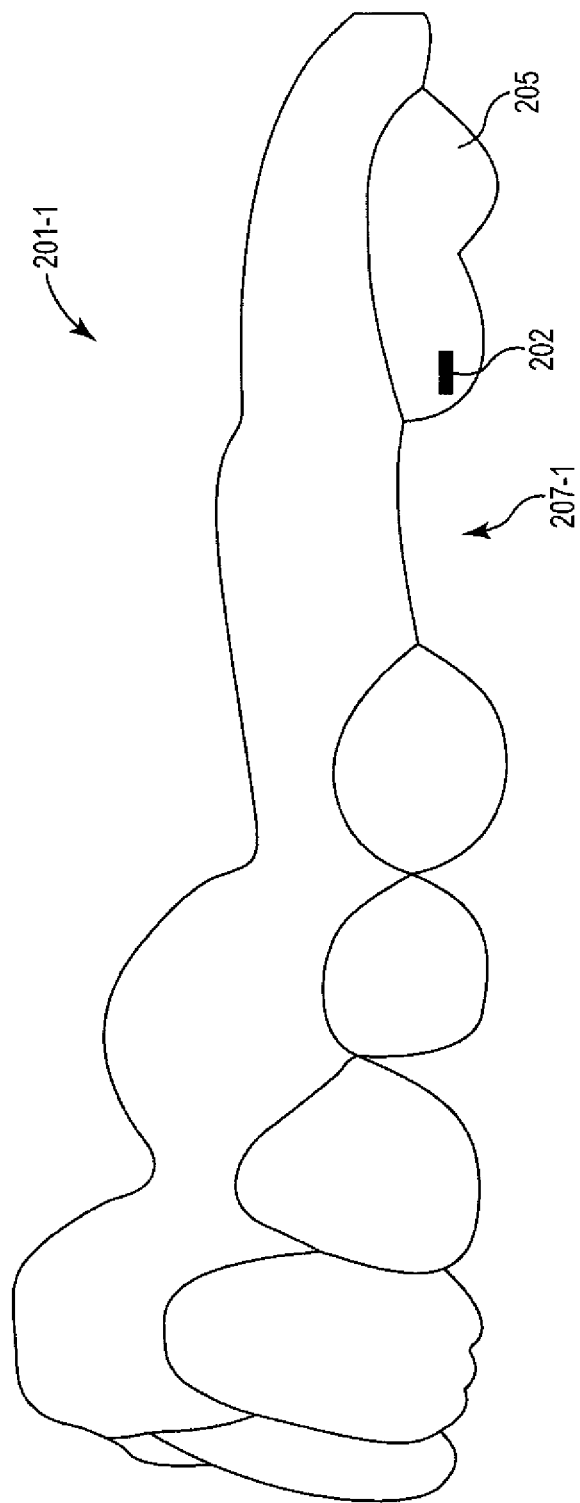

FIG. 2B illustrates upper jaw 201-1 including space 207-1. An attachment 202 can be applied to a tooth 205 of upper jaw 201-1. Attachment 202 can be used in conjunction with a shell 203-1 (see FIG. 2C) having a hook 206 and guide slot 204-1 formed therein that can serve as a guide to adjust (e.g., move) a tooth bodily.

Bodily tooth movement can include translation, for example, where all points on the tooth body move in the same direction and with the same magnitude. In bodily tooth movement, the center of rotation can effectively be an infinite distance away from the tooth because there is no rotation.

In a number of examples, the tooth 205 can be adjusted mesially to close space 207-1. As will be discussed further herein, a first end of an attachment band can be attached to attachment 202 and a second end of the band can be attached to a hook 206 of shell 203-1, for example, as illustrated in FIG. 2C.

Figure 2C:
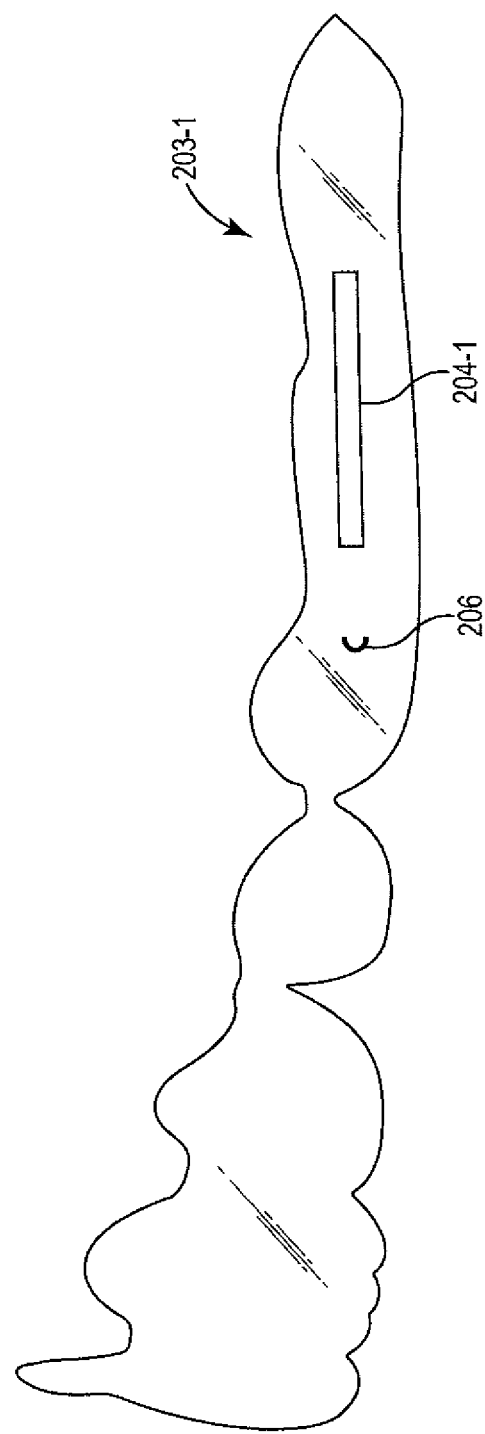

FIG. 2C illustrates a shell (e.g., dental appliance) 203-1 including a guide slot 204-1 and a hook 206. Shell 203-1 can be formed for an upper jaw, lower jaw, and/or a portion of a jaw, for example. Guide slot 204-1 can be configured to receive an attachment 202 (see FIG. 2B) and to define an adjustment trajectory of the tooth 205 (see FIG. 2B).

In a number of examples, guide slot 204-1 can control the movement of the tooth and thereby reduce or prevent a tooth from undesired movements and/or orientations (e.g., moving in an incorrect direction in one or more dimensions) during adjustment. Hook 206 can be used in conjunction with the guide slot 204-1 and an attachment 202 can be utilized to receive an end of an adjustment band, as will be discussed further herein. Hook 206 can be located on the appliance (as shown in FIG. 2C), on a tooth adjacent to space 207-1, or can be located on a tooth not adjacent to space 207-1, for example. In embodiments where the hook is located on an adjacent tooth, both of the adjacent teeth can be pulled toward the space to close it. When the hook is attached to the shell, the shell can use the other teeth on which the shell is positioned as an anchor to assist in moving the tooth having the attachment.

Hook 206 can be a number of shapes and sizes. For example, hook 206 can include a "c" shape as illustrated in FIG. 2C, a "u" shape, an irregular shape, a circular shape, and/or any variation of the shapes, among others. Hook 206 can be larger, smaller, and/or the same size as illustrated in FIG. 2D.

In a number of embodiments, guide slot 204-1 can include markings to track adjustment and/or movement of a tooth and/or teeth. In some examples, guide slot 204-1 can be configured to stop adjustment and/or movement of a tooth and/or teeth when a tooth and/or teeth reach a target position. In some examples, the guide slot and/or area (e.g., edge) around the guide slot can utilize a thicker, stronger, and/or denser material than other portions of the material of shell 203-1. In some such embodiments, this added thickness can allow for the guide slot to be used to stop movement of a tooth, for example. Such an embodiment can be accomplished by providing a sheet of material that has added thickness in some areas and then forming that material over a mold of the patient's dentition or can be formed via a non-vacuum molding process similar to formation using stereo lithographic techniques.

Figure 2D:
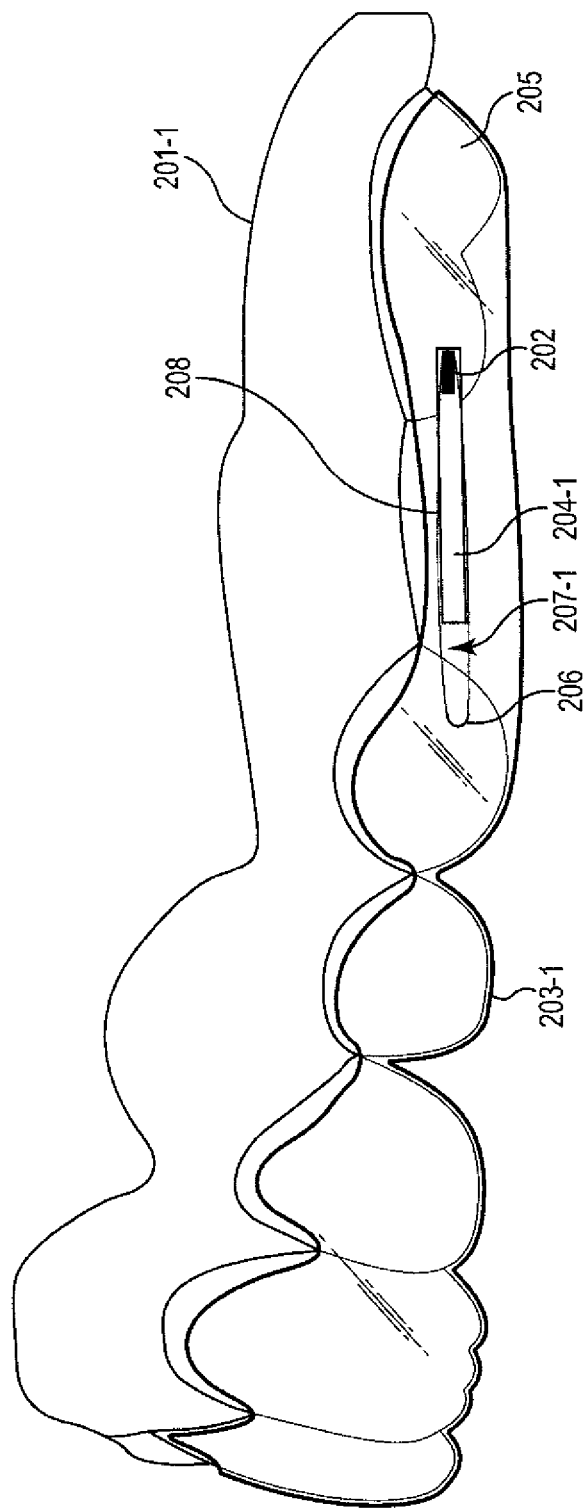

FIG. 2D illustrates upper jaw 201-1 with shell 203-1 fitted over the teeth of upper jaw 201-1. Shell 203-1, along with attachment 202, hook 206, and adjustment band 208 (e.g., an elastic band) can work in conjunction to apply force on a tooth (e.g., tooth 205) to adjust the tooth to a target position (e.g., to close gap 207-1).

In a number of examples of the present disclosure, shell 203-1 can move teeth at increased intervals and/or paces through the utilization of attachment 202, guide slot 204-1, adjustment band 208, and hook 206 with respect to other tooth movement techniques.

Tooth body movements (e.g., moving a tooth to, for example, fill a gap) can be made using shell 203-1, attachment 202, guide slot 204-1, adjustment band 208, and hook 206. For example, tooth 205 can be moved into space 207-1 to close the space to one side (e.g., tooth 205 moves mesially).

The sides of the guide slot 204-1 can be utilized to guide the attachment (and thereby, the tooth) from a present position to a target position along a target path (e.g., the direction along the length of the guide slot) and can be utilized to reduce or prevent tooth 205 from tipping from a target root/crown orientation by guiding tooth 205's adjustment trajectory, for example, in a straight sliding manner. In some examples, other individual teeth, the palette, the gingiva, and/or a dental arch (e.g., arch of the jaw) can act as an anchor through shell 203-1. Shell 203-1, for example, can include a block (e.g., integrated into shell 203-1) to stop tooth 205 from moving beyond a desired orientation.

Guide slot 204-1 can, for example, be located on a lingual side of shell 203-1, a buccal side of shell 203-1, or both sides of shell 203-1. This can be advantageous if it is desired to adjust multiple teeth or to reduce rotational or tipping force on the tooth, for example.

The interaction between attachment 202, adjustment band 208, and guide slot 204-1 can generate a number of teeth movements including, for example: reciprocal tooth movement, movement to one side, vertical movement with respect to a given tooth to create intrusion or extrusion, movement in a trajectory to change height (e.g., extrude or intrude a tooth while moving), and/or movement of a tooth along a shaped cut (e.g., to correct a tilted tooth, also called uprighting), among others. As discussed above, in a number of embodiments, adjustment can be done on a lingual side of a mouth and/or jaw and/or two or more sides (e.g., lingual and buccal) simultaneously to reduce and/or eliminate rotational forces on a tooth (e.g., tooth 205).

Figure 3:
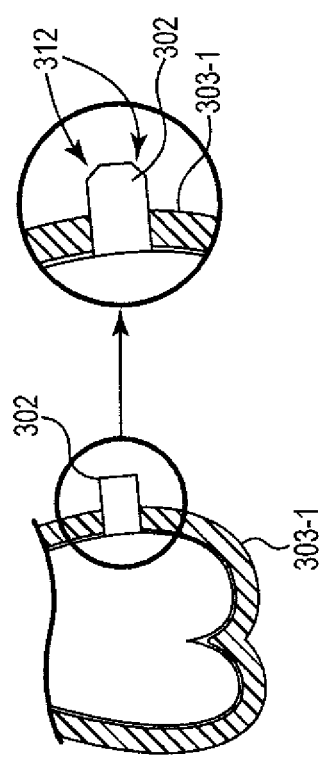
FIG. 3 illustrates an example attachment according to a number of embodiments of the present disclosure.

FIG. 3 illustrates an example attachment 302 according to a number of embodiments of the present disclosure. Attachment 302 can protrude through and beyond an outer surface of the shell (e.g., dental appliance, aligner) 303-1. As discussed above, the attachment can interact with one or more edges and/or ends of a guide slot (e.g., guide slot 204-1 of the embodiment of FIG. 2D) such that the attachment is guided along a target path toward a target position for the tooth and/or for movement to be stopped when the attachment reaches an end of the slot.

In some embodiments, attachment 302 can also include chamfered edges 312 that allow for smoother insertion, application, and/or removal of shell 303-1 over attachment 302 in contrast to straight edges. For example, shell 303-1 can be flexed over attachment 302's chamfered edges 312 to fit shell 303-1 over attachment 302.

Figure 4A:
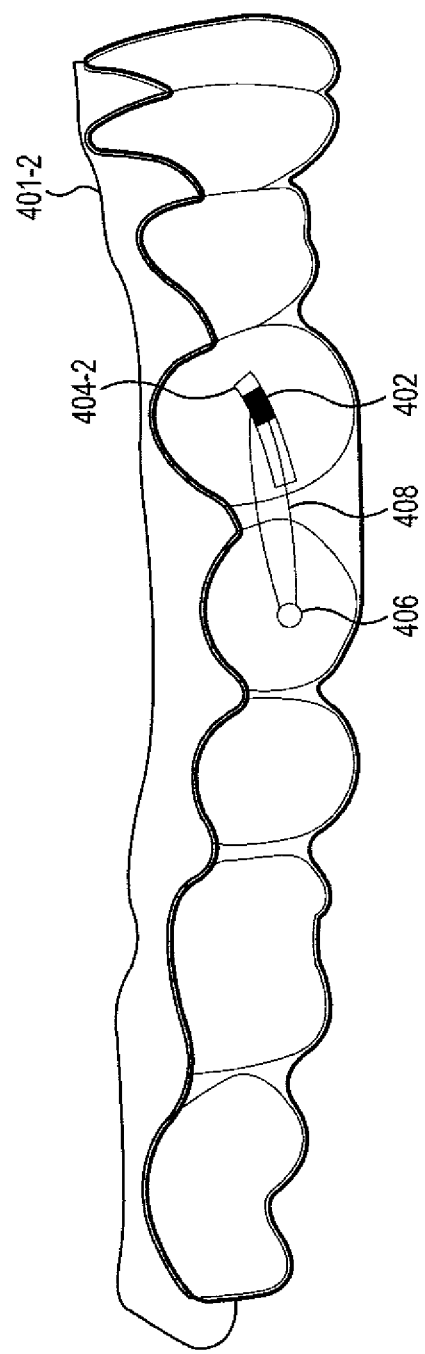
FIGS. 4A-4F illustrate alternative systems and devices for adjusting a tooth position according to a number of embodiments of the present disclosure.

FIGS. 4A-4E illustrates alternative systems and devices for adjusting a tooth position according to a number of embodiments of the present disclosure. For example, FIG. 4A illustrates an upper jaw 401-2 having a shell with a guide slot 404-2, a hook 406, a tooth attachment 402, and an adjustment band 408. In the example illustrated in FIG. 4A, guide slot 404-2 and attachment 402 are at an angled orientation with respect to each other. Such an alignment can be utilized to allow for angled tooth adjustment with respect to the orientation of the jaw. In a number of embodiments, the example illustrated in FIG. 4A can accommodate angulation, translation, uprighting, and/or can control tipping of a tooth.

Figure 4B:
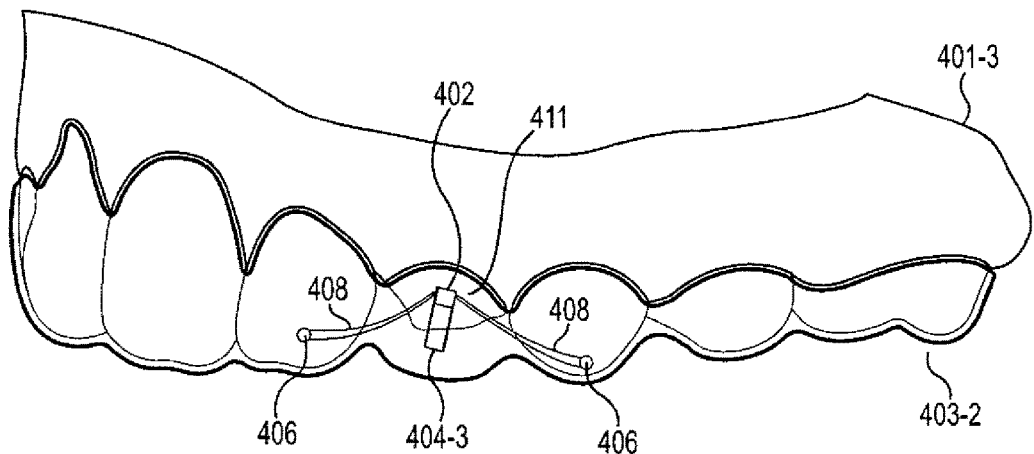

FIG. 4B illustrates an upper jaw 401-3 having a shell 403-2 with a guide slot 404-3, hooks 406, tooth attachment 402, and adjustment bands 408 positioned thereon. Guide slot 404-3 can, for example, be positioned vertically (e.g., perpendicular to a jaw), horizontally (e.g., parallel to a jaw), and/or angled (e.g., at an angle to a jaw).

A vertical and/or angled guide slot can allow for tooth extrusion (e.g., forced eruption) and/or intrusion, for example. Attachment 402 can be attached to a tooth and can extend through guide slot 404-3 and through shell 403-2, for example. Embodiments, such as that shown in FIGS. 4B and 4C, can pull a tooth down into position, or guide the tooth as it erupts such that it is moved into a correct position (e.g., in the embodiments shown, a shell having an angled guide slot moves the tooth downward and mesially).

In the embodiment illustrated in FIG. 4B, multiple (e.g., two) bands 408 are utilized. In this embodiment, a first end of an attachment band 408 is attached to a hook 406, and a second end of attachment band 408 is attached to attachment 402, for example. In such an embodiment multiple forces can be applied by the multiple bands to move the tooth with the aid of the guide slot 404-3.

In the example illustrated in FIG. 4B, tooth 411 may be damaged and/or diseased, (e.g., below the gingival line) and as a result, is targeted for extrusion. Extrusion includes an orthodontic technique for elongation or elevation of the targeted tooth and can include an orthodontic movement in a coronal direction achieved by applying a force to the targeted tooth (e.g., tooth 411). During extrusion, force can be applied to tooth 411, for example, by shell 403-2 and/or adjustment bands 408 pulling at tooth 411, and the force can further break out tooth 411 through the gingiva. Similarly, extrusion can be used to expose more of a clinical crown of a tooth and/or move a nonfunctional impacted tooth into a functional occlusion, for example.

In a number of embodiments, attachment 402 can be applied to a tooth on a dental arch opposite tooth 411. Doing so can, for example, change a direction, force, and/or other adjustment factor by the adjustment bands 408 on the tooth targeted for extrusion. Adjusting the placement of the attachment can be determined based on initial and target tooth positions of tooth 411, for example.

Figure 4C:
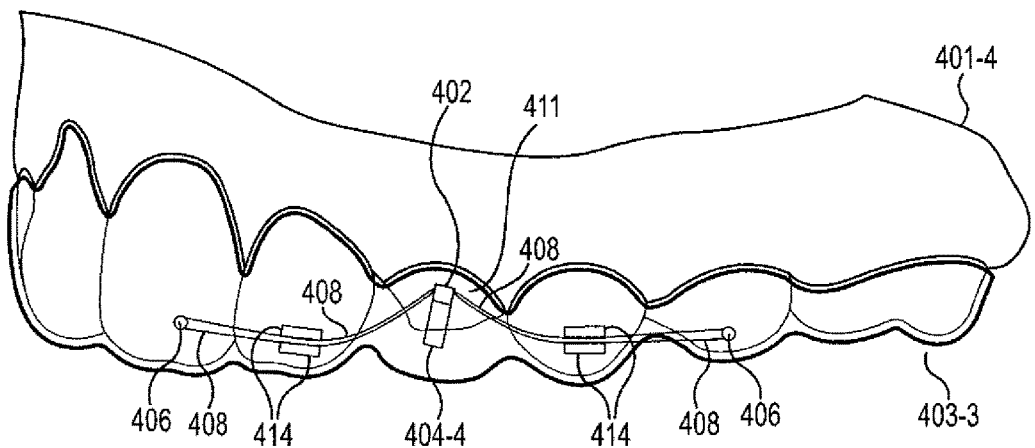

In the embodiment illustrated in FIG. 4C, multiple (e.g., two) bands 408 are utilized, along with multiple (e.g., two) protrusions 414. In this embodiment, an upper jaw 401-4 having an attachment 402 and a shell 403-3 with a guide slot 404-4, hooks 406, multiple adjustment bands 408, and multiple protrusions 414, is illustrated.

Protrusions 414 can be used to change an angle at which a band pulls the tooth. A protrusion can be any shape that acts to change the direction of an adjustment band. Protrusions can also be used to allow a force in a first direction to be applied to one or more first teeth and a force in a second direction to be applied to one or more second teeth.

In the embodiment of FIG. 4C, a first end of each attachment band 408 is attached to one of the hooks 406, and a second end of each attachment band 408 is attached to the attachment 402, for example. In such an embodiment multiple forces can be applied by the multiple bands to the tooth to move the tooth with the aid of the guide slot 404-4.

In some examples of the present disclosure, an adjustment band (e.g., an elastic chain and/or elastic band 408) along with a number of attachments can be utilized to generate targeted interproximal contacts. Interproximal contact can include one or more points of contact between adjacent teeth in the same arch. In some instances, interproximal contacts can prevent the teeth from drifting. Drifting can result in an open contact or an overly tight contact, for instance. Similarly, reaching a target interproximal contact, along with a target size and shape of the contact surface, can reduce other orthodontic issues (e.g., prevent food impaction). Embodiments of the present disclosure can be utilized to reach target interproximal contact characteristics.

A vertical and/or angled guide slot such as guide slot 404-4 can allow for tooth extrusion, for example. Attachment 402 can be attached to a tooth and can extend through guide slot 404-4 and beyond the outer surface of the shell 403-3, for example. A first end of an attachment band 408 is attached to a hook 406, and a second end of attachment band 408 is attached to and/or wrapped around attachment 402, for example. A force can be applied to a tooth targeted for extrusion, for example, by shell 403-3 and/or adjustment bands 408. In a number of embodiments, attachment 402 can be applied to a dental arch (e.g., a tooth on a dental arch) opposite the tooth to be extruded (e.g., tooth 411).

Adjustment bands 408 provide a directional force and can be any suitable material or structure. For example, adjustment bands can be made from resilient materials such as elastic, rubber, and/or other materials and can be a number of different diameters, sizes, and strengths. An adjustment band can provide different forces on a tooth based on a thickness, length, and or material used. In some embodiments, multiple adjustment bands 408 can be attached to a single attachment, hook, and/or other attachment point can be utilized.

Adjustment bands (e.g., bands 408), in a number of embodiments, can be used to increase an amount of force provided on a tooth, for example, by increasing a strength of a band or decreasing a length of a band. Similarly, in a number of embodiments, adjustment bands can be used to decrease an amount of force on a tooth by decreasing a strength of a band or increasing a length of a band, for instance.

An embodiment can include a treatment with bands of different lengths and strengths attached to a same attachment point. As treatment progresses, the force placed on a tooth can decrease from a highest level of force (e.g., multiple bands pulling) to a lowest level of force (when the longer bands are looser, and a final band is doing most and/or all of the work). Although referred to generally herein as a band, an adjustment band can have any suitable form factor that provides a suitable force for use in embodiments of the present disclosure.

Figure 4D:
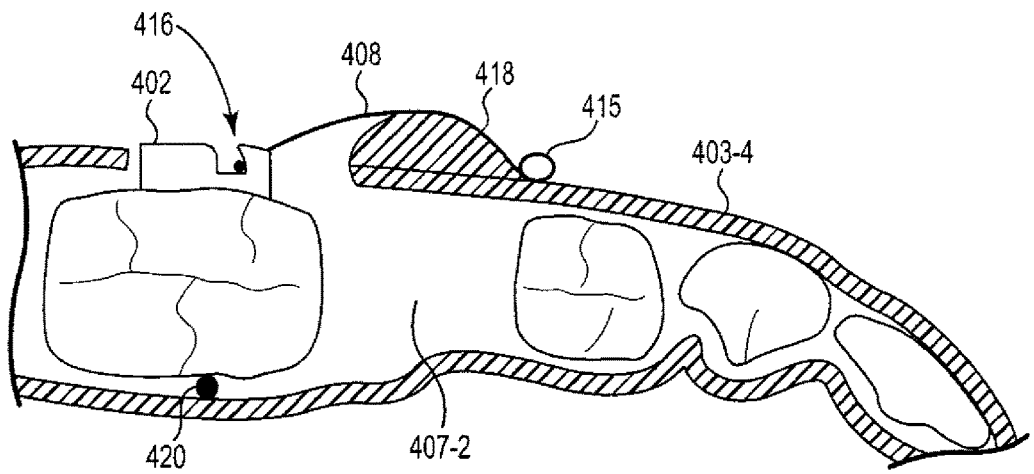

FIG. 4D illustrates an underside of an upper jaw including an empty space 407-2 where a tooth may be moved. Shell 403-4, in conjunction with adjustment band 408 can be used to adjust a tooth and/or teeth to a target position (e.g., to move the tooth into space 407-2).

In a number of embodiments, rotation (e.g., unwanted rotation) of a tooth can be reduced and/or eliminated by utilizing attachment 402 and adjustment band 408. For example, adjustment band 408 can be connected to attachment 402 in a predefined position to reduce rotation due to distance from the center of a tooth. The attachment of the band to the shell can be accomplished in any suitable manner. For example, in the embodiment of FIG. 4D, an attachment 415 is formed on the outside of the shell. The end of the band can be wrapped around this attachment 415 or, in some embodiments, the band can include a correspondingly sized loop that is sized to fit around the attachment.

Attachment 402 can include a connection point 416 that has been shaped and/or positioned in a predetermined manner to reduce (e.g., minimize) rotational force on the tooth and/or teeth and/or to increase control of the adjustment of the tooth position. As discussed above, in a number of examples, lingual and buccal attachments can be utilized simultaneously to adjust a tooth position.

In various embodiments, as illustrated in FIG. 4D, dimples 420 can be attached to a tooth to reduce (e.g., minimize) rotational force on the tooth and/or teeth. For example, dimples 420 can include bumps that change the shape of the tooth and that interact with the surface of the shell, and thus can change the directional movement of the tooth (e.g., reduce rotation force on the tooth). In some embodiments, dimples can be placed on the shell or formed integrally with the shell.

In some examples to reduce tooth rotation, a bulge 418 can be added to shell 403-4 to change the angle at which the band interacts with the attachment. Such features can be utilized, for example, to reduce rotation due to the feature's distance from the center of a tooth. Additional dimples and/or bulges, for example, can be added to a lingual side of a tooth to resist a rotation of the tooth.

Figure 4E:
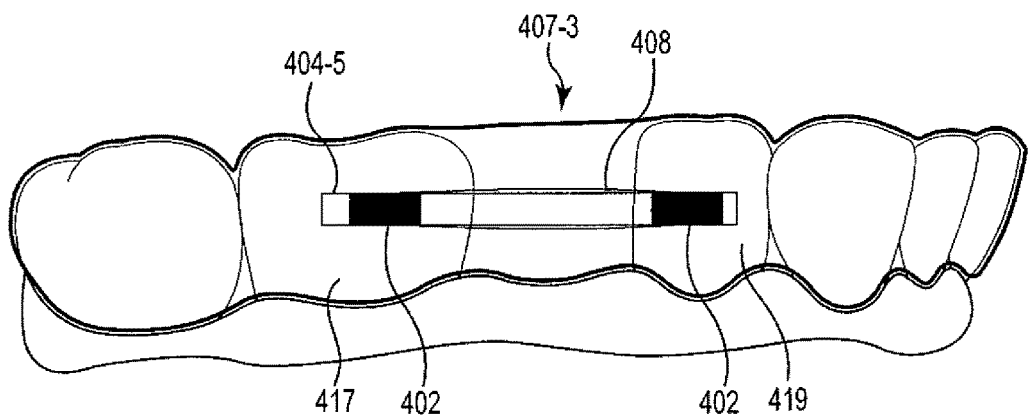

FIG. 4E illustrates a jaw having a guide slot 404-5, attachments 402, and adjustment band 408 positioned thereon. In a number of embodiments, two or more attachments 402 can be utilized to move a tooth and/or teeth, for example, into a tooth space 407-3. For example, teeth 417 and 419 can undergo reciprocal tooth movement to close space 407-3. Reciprocal tooth movement can include two teeth (e.g., teeth 417 and 419) or resistance units of similar or equal size pulling against each other to close a space (e.g., the reciprocal closure of a maxillary midline diastema). In a number of embodiments, a first tooth (e.g., tooth 417) can remain idle, while a second tooth (e.g., tooth 419) is moved toward the first tooth to close a space (e.g., space 407-3). In some embodiments, both teeth can be moved during the same period of time.

Figure 4F:
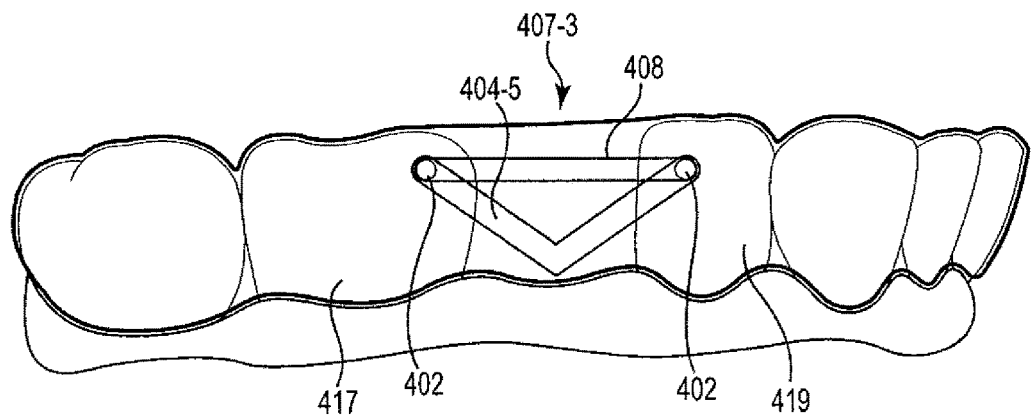

FIG. 4F illustrates a jaw having a v-shaped guide slot 404-5, attachments 402 on two teeth adjacent to a space, and adjustment band 408 positioned around the two attachments. As illustrated in this embodiment, in a number of embodiments, two or more attachments 402 can be utilized to move a tooth and/or teeth, for example, into a tooth space 407-3.

For example, teeth 417 and 419 can undergo tooth movement to close space 407-3. In this embodiment, the V-shaped slot provides some downward force that can work to pull the top of the tooth downward as the tooth is being pulled into the space 407-3. Such an embodiment can be used if a tooth is in need of straightening as well as movement to close the space. This embodiment is illustrative of other configurations that could be utilized to adjust tooth orientation while moving one or more teeth and although it shows one type of movement being addressed, it should be understood that other embodiments may address other types of movement.

Figure 5:
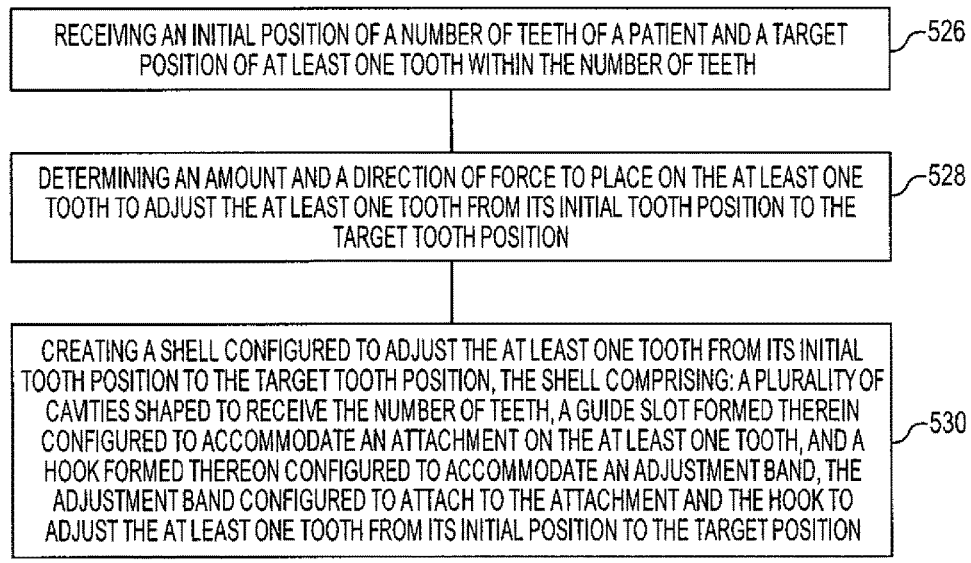
FIG. 5 illustrates a method for adjusting a tooth position according to a number of embodiments of the present disclosure.

FIG. 5 illustrates a method 524 for adjusting a tooth position according to a number of embodiments of the present disclosure. Adjusting a tooth position may be desirable in a number of situations, including, for example, to close a space between teeth, to achieve target interproximal contacts, to generate space for an implant, to generate space for an un-erupted tooth, to adjust/move a tooth in a target trajectory, and/or to upright, extrude, adjust, and/or move a tooth to a target (e.g., predefined) location, among others.

At 526, an initial position of a number of teeth of a patient and a target position of at least one tooth within the number of teeth is received. For example, an initial tooth position may include a misaligned tooth to be adjusted, uprighted, and/or extruded, among others. A target position can include a position determined by a treatment professional (e.g., orthodontist) or other specialist. The target position can include the position where the tooth should be post-treatment. A shell manufacturer can receive this information for use in designing a shell and/or adjustment bands for use in adjusting a tooth position.

At 528, an amount and a direction of force to place on the at least one tooth to adjust the at least one tooth from its initial tooth position to the target tooth position is determined. This can be determined by a shell manufacturer and/or treatment professional, for example. The amount and direction of the force can be determined based on what is needed to adjust (e.g., move) the tooth from an initial position to a target position. This adjustment can take place in one or more treatment stages, for example.

At 530, a shell configured to adjust the at least one tooth from its initial tooth position to the target tooth position is designed. The shell can comprise, for example, a plurality of cavities shaped to receive the number of teeth, a guide slot formed therein configured to accommodate an attachment on the at least one tooth, and a hook formed thereon configured to accommodate an adjustment band, the adjustment band configured to attach to the attachment and the hook to adjust the at least one tooth from its initial position to the target position.

The shell can be configured to use a patient's upper and/or lower dental arch as an anchor, allowing for movement of the teeth as a group, with the shell. The shell's guide slot can serve as a guide slot between the tooth and/or teeth and the attachment. The guide slot can govern how and where the tooth moves (e.g., the tooth can only move along constraints of the guide slot).

In a number of embodiments, adjusting a tooth position can include adjusting a tooth vertically or horizontally with respect to a given tooth. For example, the guide slot in the shell and/or the attachment can be oriented vertically or horizontally with respect to a given tooth based on the target position of the tooth to be adjusted.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for moving at least one tooth within a number of teeth, comprising:
   receiving, from a treatment professional, an initial position of a number of teeth of a patient and a target position of the at least one tooth within the number of teeth;
   determining an amount and a direction of force to place on the at least one tooth based on the initial position and the target position; and
   creating a dental appliance configured to adjust the at least one tooth from the received initial position to the target position, the dental appliance comprising:
      a plurality of cavities shaped to receive the number of teeth, wherein the plurality of cavities include a first and second side wall;
      a guide slot formed in the first side wall and configured to accommodate an attachment on the at least one tooth; and
      a hook located on the first side wall and configured to accommodate an adjustment band.

2. The method of claim 1, wherein the method includes adjusting the at least one tooth from the initial position to the target position by the adjustment band, wherein the adjustment band is attached to the attachment and the hook.

3. The method of claim 1, wherein the method includes marking the guide slot to track adjustment of the at least one tooth.

4. The method of claim 1, wherein the method includes determining the size of the guide slot based on an adjustment distance needed to reach the target position.

5. The method of claim 1, wherein the method includes adjusting the orientation of the guide slot, attachment, and hook in accordance with the target position.

6. The method of claim 1, wherein the method includes constraining movement of the at least one tooth along the guide slot.

7. The method of claim 1, wherein the method includes determining the amount and the direction of force to adjust the at least one tooth from the initial position to the target position.

8. A method for moving at least one tooth within a number of teeth, comprising:
   receiving, from a treatment professional, an initial position of a number of teeth of a patient and a target position of at least one tooth within the number of teeth;
   determining, based on the initial position and the target position, an amount and a direction of force to place on the at least one tooth to adjust the at least one tooth from the initial position to the target position;
   creating a dental appliance configured to adjust the at least one tooth from the received initial position to the target position, the dental appliance comprising:
      a plurality of cavities shaped to receive the number of teeth, wherein the plurality of cavities include a first and second side wall;
      a guide slot formed in the first side wall and configured to accommodate an attachment on the at least one tooth; and
      a hook located on the first side wall and configured to accommodate an adjustment band, wherein the adjustment is band configured to attach to the attachment and to the hook to generate a force on the at least one tooth to adjust the at least one tooth from the initial position to the target position; and
   adjusting the at least one tooth from the initial position to the target position via the dental appliance and the adjustment band, wherein the adjustment band is attached to the attachment and the hook of the dental appliance.

9. The method of claim 8, wherein adjusting the at least one tooth includes adjusting the at least one tooth vertically with respect to a given tooth via the guide slot, wherein the guide slot has an angled orientation with respect to a jaw of the patient.

10. The method of claim 8, wherein adjusting the at least one tooth includes adjusting the at least one tooth horizontally with respect to a given tooth via the guide slot, wherein the guide slot has a perpendicular orientation with respect to a jaw of the patient.

11. The method of claim 8, wherein the method includes adjusting the at least one tooth from the initial position to the target position in a plurality of treatment stages.

12. The method of claim 8, wherein the method includes guiding the attachment on the at least one tooth along a target path for movement of the at least one tooth from the initial position to the target position.

13. The method of claim 8, wherein adjusting the at least one tooth from the initial position to the target position includes reducing rotational force on the at least one tooth via a dimple that changes the shape of the at least one tooth, wherein the dimple is at least one of:
attached to the at least one tooth;
placed in the dental appliance; and
formed integrally with the dental appliance.

14. A method for moving at least one tooth within a number of teeth, comprising:
receiving, from a treatment professional, an initial position of a number of teeth of a patient and a target position of at least one tooth within the number of teeth;
determining, based on the initial position and the target position, an amount and a direction of force to place on the at least one tooth to adjust the at least one tooth from the initial position to the target position; and
creating a dental appliance configured to adjust the at least one tooth from the received initial position to the target position, the dental appliance comprising:
a plurality of cavities shaped to receive the number of teeth, wherein the plurality of cavities include a first and second side wall;
a guide slot formed in the first side wall and configured to accommodate an attachment on the at least one tooth; and
a hook located on the first side wall and configured to accommodate an adjustment band, wherein the adjustment band is configured to generate force on the at least one tooth for movement of the tooth to the target position; and
adjusting the at least one tooth from the initial position to the target position via the dental appliance and the adjustment band, wherein the adjustment band is attached to the attachment and the hook of the dental appliance.

15. The method of claim 14, wherein the method includes closing a space between the at least one tooth and a different tooth of the number of teeth by adjusting the at least one tooth from the initial position to the target position via the dental appliance and the adjustment band.

16. The method of claim 14, wherein adjusting the at least one tooth includes generating a space between the at least one tooth and a different tooth of the number of teeth for an implant.

17. The method of claim 14, wherein adjusting the at least one tooth includes generating a space between the at least one tooth and a different tooth of the number of teeth for an un-erupted tooth.

18. The method of claim 14, wherein adjusting the at least one tooth includes uprighting the at least one tooth.

19. The method of claim 14, wherein adjusting the at least one tooth includes extruding the at least one tooth.

20. The method of claim 14, wherein the method includes adjusting the at least one tooth from the initial position to the target position to achieve a target interproximal contacts.

* * * * *